(12) United States Patent
Farin et al.

(10) Patent No.: US 6,197,026 B1
(45) Date of Patent: Mar. 6, 2001

(54) ELECTROSURGICAL INSTRUMENT

(75) Inventors: Günter Farin; Karl Ernst Grund, both of Tübingen (DE)

(73) Assignee: Erbe Elektromedizin GmbH (DE)

( * ) Notice: Subject to any disclaimer, the term of this patent is extended or adjusted under 35 U.S.C. 154(b) by 0 days.

(21) Appl. No.: 09/351,034

(22) Filed: Jul. 9, 1999

(51) Int. Cl.⁷ .................................................. A61B 18/18
(52) U.S. Cl. ........................... 606/49; 606/40; 219/121.5
(58) Field of Search ................................ 606/27, 28, 40, 606/41, 45, 46, 48–50; 219/121.5, 121.51

(56) References Cited

U.S. PATENT DOCUMENTS

| 5,207,675 | * | 5/1993 | Canady . |
| 5,239,161 | | 8/1993 | Lang ................................... 219/121.5 |
| 5,720,745 | | 2/1998 | Farin et al. ............................. 606/49 |
| 6,039,736 | | 3/2000 | Platt, Jr. ................................. 606/49 |

FOREIGN PATENT DOCUMENTS

| 41 39 029 A1 | * | 6/1993 | (DE) . |
| 0 956 827 | | 11/1999 | (EP) . |

OTHER PUBLICATIONS

Farin, Günter and K.E. Grund. "Technology of Argon Plasma Coagulation with Particular Regard to Endoscopic Applications. " *Endoscopic Surgery and Allied Technologies*, No.1, vol. 2. New York: Georg Thieme Verlag (Feb. 1994).

Grund, Karl Ernst et al. "Endoscopic Argon Plasma Coagulation (APC) First Clinical Experiences in Flexible Endoscopy. " *Endoscopic Surgery and Allied Technologies*, No. 1, vol. 2. New York: Georg Thieme Verlag (Feb. 1994).

* cited by examiner

*Primary Examiner*—Michael Peffley
(74) *Attorney, Agent, or Firm*—St. Onge Steward Johnston & Reens LLC

(57) ABSTRACT

Electrosurgical instruments for the coagulation of biological tissue are known that comprise a gas source to supply an inert gas, in particular a noble gas, to at least one outflow opening as well as an HF source to supply a coagulation current to an electrode device that is disposed in the region of the at least one outflow opening. It is proposed to make the outflow opening slit-shaped in such a way that the inert gas emerges in a flat or fan-shaped stream, which in its marginal regions flows laminarly so that the inert gas reaches the tissue substantially without becoming mixed with ambient air.

15 Claims, 2 Drawing Sheets

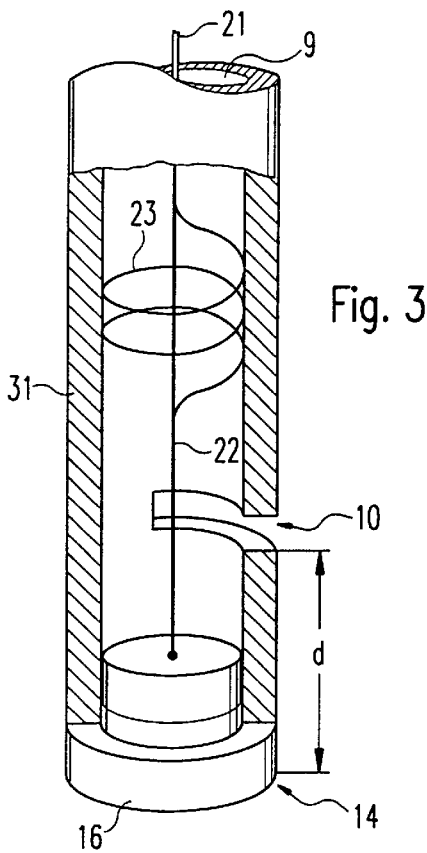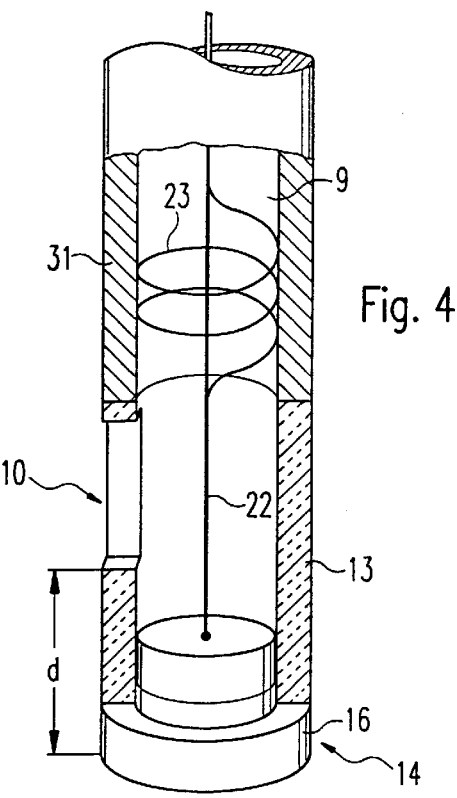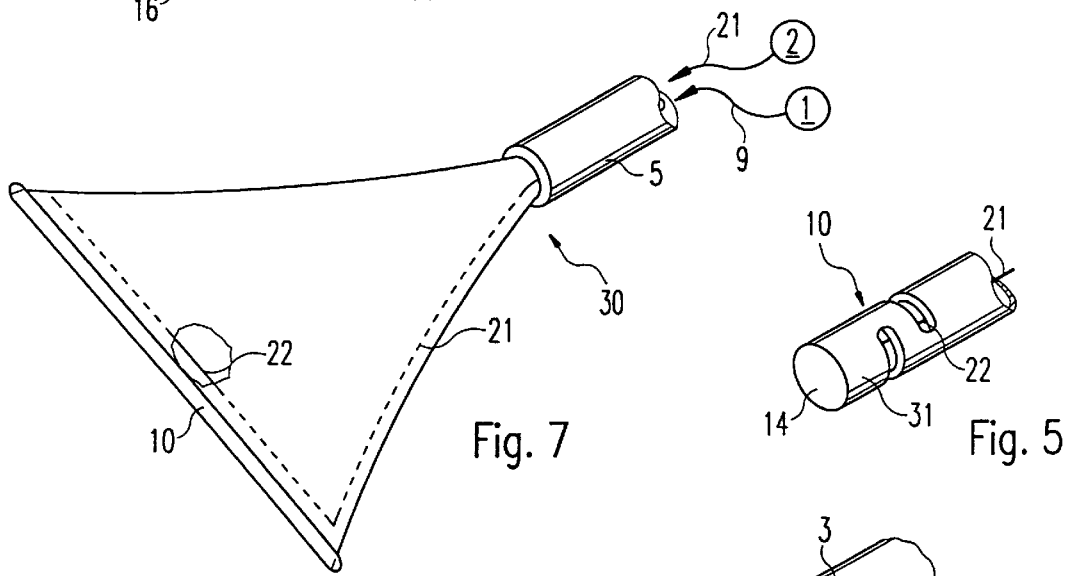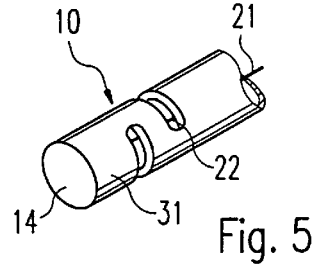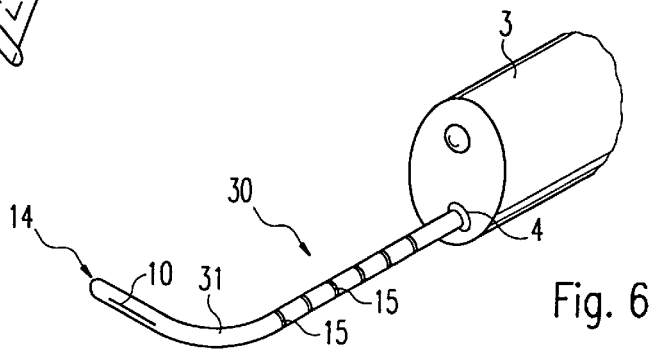

ELECTROSURGICAL INSTRUMENT

BACKGROUND OF THE INVENTION

The invention relates to an electrosurgical instrument for the coagulation of biological tissues.

Plasma surgery is a method of monopolar high-frequency surgery (HF surgery) in which a high-frequency electrical current (HF current) produced by a high-frequency generator (HF generator) is sent through an ionized noble gas (plasma), for example argon (argon plasma), from an electrical pole within a suitable surgical instrument onto the tissue to be treated and from there is conducted back to the HF generator through a so-called neutral electrode applied to the patient (G. Farin et al.: Technology of Argon Plasma Coagulation with Particular Regard to Endoscopic Applications; Endoscopic Surgery and Allied Technologies, No. 1, Vol. 2, February 1994, 71–77). As a result heat is introduced to the tissue, both endogenously by the HF current and exogenously by the higher temperature of the plasma relative to the tissue, so that the temperature of the tissue rises. Depending on the temperature various thermal effects are caused in the tissue, which can be used by surgeons for various therapeutic purposes such as blood coagulation or hemostasis and/or the thermal devitalization or destruction of pathological tissues (K. E. Grund et al.: Argon Plasma Coagulation in Flexible Endoscopy, Endoscopic Surgery and Allied Technologies, No. 1, Vol. 2, February 1994, 42–46).

A substantial physical prerequisite for plasma surgery is a noble gas, such as the aforementioned argon or helium, which must be present between the electrical pole formed by an electrode within the instrument and the tissue to be treated. The reason is that noble gases can be ionized with relatively low electrical field strengths in comparison to oxygen and/or nitrogen or air, and they do not react chemically with the tissue. Hence the tissue is not carbonized or even vaporized.

Within the last five years plasma surgery, in particular in the course of flexible endoscopy, has found a broad indication spectrum (K. E. Grund: DMW), so that a variety of demands are made with respect to the application techniques and the instruments, HF generators and gas sources required.

The U.S. Pat. No. 5,207,675 discloses an electrosurgical instrument that is problematic inasmuch as the electrode of the instrument can unintentionally come into direct contact with the tissue. Because of the relatively high HF voltage at the electrode, there is thus a risk that in particular thin-walled organs, such as those that are ordinarily present in the gastrointestinal tract and in the tracheobronchial system, may be perforated.

The patent DE 41 39 029 A1 discloses an electrosurgical instrument in which the electrode is disposed within the instrument in such a way that it does not touch the tissue, as long as the instrument is used according to instructions. A problem with this instrument is that the noble gas flows out of one or several openings at the distal end of the instrument in a predetermined direction. As a result the HF current can also flow to the tissue only in this directed (ionized) gas stream. When large-area lesions are to be treated this is disadvantageous inasmuch as the instrument must be moved several times over the tissue to be treated in order that the HF current and thus also the intended thermal effects are applied as uniformly as possible over the entire large area of the lesion.

In DE 195 35 811 C1 an electrosurgical instrument of the kind cited above is disclosed in which a diffusor is provided at the gas outlet, which is intended to prevent a mechanical action on liquid and tissue. In particular during the treatment of large-area lesions, however, it has been found that as a result of the unavoidable or even desired turbulences in the current of noble gas, mixing of the noble gas with the ambient gas (which as a rule is air) occurs, so that the specific advantages of plasma surgery are partially abolished.

SUMMARY OF THE INVENTION

The object of the invention is to develop a surgical instrument of the kind cited above further in such a way that the treatment of even large-area lesions is improved.

More particularly, the invention is an electrosurgial instrument for the coagulation of biological tissue, comprising a body including at least one outlet opening, and a gas source to supply an inert gas, in particular a noble gas, to the at least one outlet opening. The outflow opening is constructed in the shape of a slit so that the inert gas emerges in a flat laminar stream, so that the inert gas arrives at the tissue substantially without becoming mixed with ambient air. The instrument also further includes an HF source to supply a coagulation current to an electrode device disposed in the region of the at least one outflow opening.

One of the principle features of this invention is the provision of an electrosurgical instrument that on one hand forms a fan-shaped stream of noble gas and on the other hand structures this stream so that mixing with ambient air practically does not occur. At the same time the gas pressure is so regulated by the invention as to avoid blowing liquid away from the tissue and to prevent the gas from entering an open blood vessel. These measures ensure that large-area lesions can be rapidly treated by a relatively slight gas stream, while still avoiding the above-mentioned danger of tissue destruction.

Preferably the electrode devices comprise at least one electrode that is disposed in the region of the outflow opening in such a way as reliably to avoid direct touching of the tissue by the electrode. Preferably in addition the electrode should be such as reliably to prevent an ignition of an arc or plasma in an inert gas contaminated by ambient air or even in air alone, both of which would be associated with the negative effects cited above.

The electrode devices comprise at least one electrode that is disposed at a substantially uniform distance from substantially all regions of the outflow opening. This feature ensures that if a uniform distance is maintained between outflow opening and tissue, a uniform band of plasma is produced, which in turn has a uniform action on the tissue to be treated.

The outflow opening is preferably so shaped and/or arranged that the pressure of the emerging inert gas is constant over substantially the entire cross section of the outflow opening. The result is, first, that a particularly uniform gas stream is produced, in which turbulence and stream deformations are avoided owing to the absence of pressure differences within the gas; on the other hand, it is ensured that all regions of the gas stream impinge "gently" on the tissue, so that a uniform plasma production is ensured.

The outflow opening is preferably so shaped and positioned on the instrument that the contact area of the stream is substantially perpendicular to a main direction of movement of the instrument. As a result, a large lesion can be treated in a minimal number of movement sequences.

The cross section of the outflow opening is preferably small in relation to the cross section of a gas-supply conduit through which the inert gas is delivered from the gas source to the outflow opening. This measure minimizes the pressure gradients within the region of the ouflow opening.

The outflow opening in one preferred embodiment of the invention is surrounded by ceramic material. Particularly in the case of re-usable probes, this ensures that no changes in shape of the outflow opening occur during use.

It is especially preferred to construct the instrument as a tubular probe and to use it in endoscopic operations in which the probe is passed through a working channel of an endoscope.

The outflow opening in this case is preferably disposed at the outer circumference of the probe at a distance from its distal end, i.e. opposite the gas source. This distance of the outflow opening from the distal end of the probe does not only offer advantages with respect to flow technology; rather, it is also an advantage for the person operating the instrument if the opening is not quite at the distal end.

In one embodiment of the invention the outflow opening is so constructed that it extends substantially parallel to the long direction of the probe. In this case the operation is carried out with a rotary movement of the endoscope, which moves the outflow opening with its long dimension transverse to the movement direction.

In another embodiment of the invention the outflow opening runs substantially around the probe in its circumferential direction. Thus the endoscope, including the probe, can be pushed forward and pulled back at the site to be treated, so that a large-area lesion can be treated with few movements.

In an alternative embodiment the outflow opening is so constructed that it spirals around the probe like a screw thread, through a circumferential angle of substantially 360° or even more. This arrangement makes it possible to achieve a substantially simultaneous treatment of a tubular hollow organ over its entire circumference.

The electrode of the probe preferably takes the form of a wire, which at least in the region of the outflow opening runs substantially in the middle of the probe and, passing by the outflow opening, is held by one end at the distal end of the probe so that it is insulated. It is thereby ensured that the electrode is at a uniform distance from the opening over the entire cross section of the latter. Separate devices of whatever kind for the purpose of improving a discharge, such as are provided for example according to U.S. Pat. No. 5,207,675, are thus not present in this embodiment of the invention.

The probe itself preferably exhibits at its distal end, where the outflow opening is also provided, annular markings disposed at equal distances from one another. In this way it is possible to estimate the distances or the degree of projection of the probe from the working channel of the endoscope in the endoscope's field of view. In addition there are preferably provided means of keeping the probe fixed in the working channel of the endoscope, so that the endoscope with the projecting probe forms an instrument that can be manipulated as a unit.

Additional characteristics of the invention will be apparent from the subordinate claims and the following description of preferred embodiments, explained in detail with reference to drawings.

BRIEF DESCRIPTION OF THE DRAWINGS

FIG. 3 shows a longitudinal section through the probe according to FIG. 1, FIG. 4 shows a longitudinal section through the probe according to FIG. 2, FIG. 5 shows a perspective view of an end section of a probe according to another embodiment, FIG. 6 shows a perspective view of an end section of an endoscope with projecting probe according to a further embodiment of the invention, and FIG. 7 shows an instrument for open surgery according to another embodiment of the invention.

In the following description, the same reference numerals are used for identical parts or parts with identical actions.

DESCRIPTION OF THE PREFERRED EMBODIMENTS OF THE INVENTION

Figure 1:
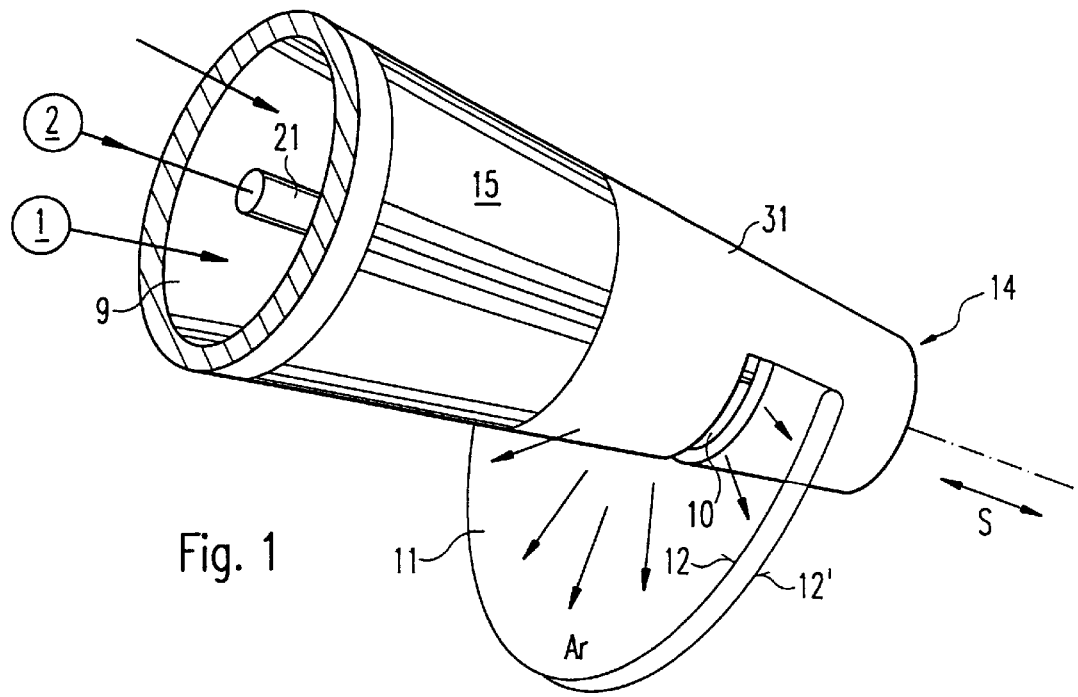
FIG. 1 shows the perspective view of an end section of one embodiment of a probe.

The embodiment of the invention shown in FIG. 1 comprises a tubular body or probe 31, the interior space or lumen of which forms a gas-supply conduit 9 connected to a gas source 1, which supplies in particular a noble gas such as argon or also helium in the direction indicated by the associated arrow. In the interior of the probe 31 a wire-shaped current conductor 21 is provided, which is connected to an HF source 2 in a manner known per se.

At the outer circumference of the probe 31 a marker ring 15 is visible, which (together with additional marker rings not shown here) despite the distorted imaging in the field of view of an endoscope provides the user with a measure of the extent to which the probe 31 is projecting from a working channel of the endoscope.

The distal end 14 of the probe 31 is, as can be seen in particular in FIG. 3, closed by an end piece 16. At a distance d from the distal end 14 or the end surface of the end piece 16 an outflow opening 10 is provided, which in the embodiment shown in FIGS. 1 and 3 passes around the probe through a circumferential angle of about 180°.

The wire-shaped current conductor 21 is held at its distal end, i.e. its end opposite the HF source 2, in the middle of the end piece 16. Ahead of the outflow opening 10 the wire-shaped current conductor 21 is kept in the center of the probe 31 by a holder 23, such that between the holder 23 and the end piece 16 an electrode 22 is produced, which is positioned substantially exactly in the center of the probe, equidistant from all regions of the outflow opening 10.

The cross section of the gas-supply conduit 9 is made sufficiently large with respect to the cross section of the outflow opening 10 that the pressure is substantially the same everywhere in the region of the outflow opening 10. By this means, and by the precise shaping of the edge regions of the opening 10, it is ensured that there emerges from the opening 10 a gas stream 11 that has substantially the shape of a section of a disk. Because of the laminarity of the gas stream 11, marginal regions 12, 12' of the gas stream 11 consist of pure gas or argon just like the interior of the stream 11, essentially unmixed with the surrounding atmosphere. When the probe 31 is moved along the arrow S (FIG. 1), therefore, a large-area lesion can be reliably treated in a few passes. In particular, of course, this applies to lesions of a concave section of tissue.

Figure 2:
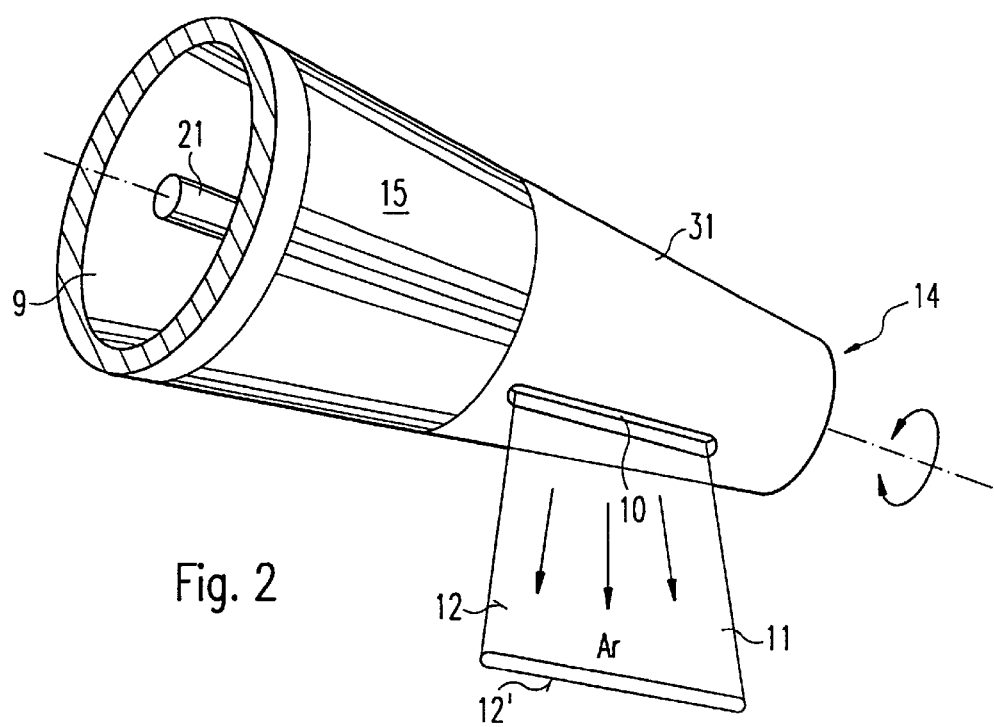
FIG. 2 shows a view like that in FIG. 1 but of another embodiment of the probe.

Another embodiment of the invention, as shown in FIGS. 2 and 4, differs from that according to FIGS. 1 and 3 in particular with respect to the shape and arrangement of the outflow opening 10. In this embodiment the outflow opening 10 has the form of a straight line; that is, it is parallel to the axis of the probe 31. Here, again, it is ensured that the electrode 22 maintains a constant distance from the outflow opening 10. Owing to this constancy of distance as well as the special configuration of the gas stream, which arrives at the tissue with no admixture of ambient atmosphere, it is ensured that not only is there no contact between the electrode 22 and the tissue to be treated, but in addition that there is practically no possibility that a plasma will be ignited in an ambient gas containing atmospheric oxygen.

The movement direction of the probe shown in FIGS. 2 and 4 corresponds to rotation about the long axis of the probe 31, as indicated in FIG. 2 by a double-headed arrow.

A further difference of the embodiment shown in FIG. 4, in comparison with that according to FIGS. 1 and 3, is that the end section of the probe 31 comprises a ceramic section 13, in which the outflow opening 10 is formed and which is fixedly connected to the tubular probe section, i.e. the wall of the gas-supply conduit 9. This feature, which of course can find application in all the embodiments shown here, ensures that even when the probe is used several times no changes in the material or the shape of the section can occur as a result of elevated temperatures. Moreover, with the processes in common use today very precise shapes can be produced in ceramic material, in particular with reference to the outflow opening 10.

Another embodiment of the invention, as shown in FIG. 5, differs from the embodiments previously described in that the outflow opening 10 spirals completely around the probe 31 like a screw thread. As a result a gas stream is produced that has substantially the shape shown in FIG. 1 but extends all the way around the probe. Particularly in the case of relatively narrow hollow organs, with such a probe it is possible to treat a circumferential lesion in a single step.

In the embodiment shown in FIG. 6 the endoscope 3 with its working channel 4 is also indicated. The probe 31 shown there, which thus constitutes a surgical instrument 30, is curved at its end ahead of the outflow opening 10. Because of the elasticity of the tubular probe 31, which for example consists of PTFE, this probe can nevertheless be inserted into the working channel 4, first straightening itself out. Not until it emerges from the working channel 4 does it resume the shape shown in FIG. 6. The basic idea here is thus that the probe can be given a shape optimized for the particular purpose of the treatment, by preforming it appropriately.

In the embodiment of the invention shown in FIG. 7 no probe is shown but rather an instrument 30 for open surgery. The outflow opening 10 is here situated in a funnel shaped end piece held by a handle 5. Here, again, the outflow opening 10 is elongated and flat. The electrode 22 is further inward, a certain distance away from but parallel to the outflow opening 10, so that large-area lesions can be treated very uniformly. The instrument 30 is guided in such a way that the outflow opening 10 and hence also the electrode 22 are moved substantially parallel to the tissue to be treated.

In another embodiment of the invention, not shown here, a small metal tube is set into the interior of the tubular probe. This serves on one hand as electrode and on the other, it brings about a cooling. For this purpose the metal tube has a low thermal resistance and is made sufficiently long that the heat generated in the region of the electrode and the slit is carried away by the gas flowing through the metal tube, far enough that the temperature does not reach a level damaging to the plastic material.

In the manufacture of the probe, the metal tube connected to the current conductor is pushed into the tubular probe, the probe is clamped and the slitlike outflow opening is made by sawing through the wall of the probe and the metal tube. Thereafter the probe is completed by closing the end. In this way the material of the metal tube ends flush with the plastic material in the outflow opening, so that here, again, no direct touching of the tissue can take place and the uniformity of the distance from the electrode to the opening is ensured.

What is claimed is:

1. Electrosurgical instrument for the coagulation of biological tissue, comprising a body including at least one outlet opening, a gas source to supply an inert gas, in particular a noble gas, to said at least one outlet opening;

an HF source to supply a coagulation current to an electrode device disposed in the region of the at least one outflow opening, wherein the outflow opening is constructed in the shape of a slit so that the inert gas emerges in a flat laminar stream, so that the inert gas arrives at the tissue substantially without becoming mixed with ambient air.

2. Electrosurgical instrument according to claim 1, wherein the electrode device comprises at least one electrode that is disposed in the region of the outflow opening within said body for avoiding direct touching of the tissue by the electrode.

3. Electrosurgical instrument according to claim 1, wherein the electrode device comprises at least one electrode that is spaced from the outflow opening for avoiding an ignition of an arc or plasma in a gas mixture ambient air or even in air alone.

4. Electrosurgical instrument according to claim 1, wherein the electrode device comprises at least one electrode that is at a substantially uniform distance from substantially all regions of the outflow opening.

5. Electrosurgical instrument according to claim 1, wherein the outflow opening is symmetrically and uniformly arranged to keep the pressure of the outflowing inert gas being constant over substantially the entire cross section of the outflow opening.

6. Electrosurgical instrument according to claim 1, wherein the outflow opening is so shaped and disposed on the instrument that the contact area of the laminar inert gas stream is substantially perpendicular to a main direction of movement of the instrument.

7. Electrosurgical instrument according to claim 1, wherein the cross section of the outflow opening is small in relation to the cross section of a gas-supply conduit to conduct the inert gas from the gas source to the outflow opening.

8. Electrosurgical instrument according to claim 1, wherein the gas outflow opening is surrounded by ceramic material.

9. Electrosurgical instrument according to claim 1, wherein the electrosurgical instrument comprises a substantially tubular probe that can be passed through a working channel of an endoscope.

10. Electrosurgical instrument according to claim 9, wherein the outflow opening is disposed at the outer circumference of the probe at a distance from its distal end opposite the gas source.

11. Electrosurgical instrument according to claim 9, wherein the outflow opening is so formed that it runs substantially parallel to the long dimension of the probe.

12. Electrosurgical instrument according to claim 9, wherein the outflow opening is so formed that it runs substantially in the circumferential direction of the probe.

13. Electrosurgical instrument according to claim 9, wherein the outflow opening is so formed that it spirals around the probe like a screw thread, through a circumferential angle of substantially 360° or more.

14. Electrosurgical instrument according to claim 9, wherein the electrode comprises a wire kept substantially in the center of the probe, at least in the region of the outflow opening, is held by one end at the distal end of the probe.

15. Electrosurgical instrument according to claim 9, where mixing means are provided to fix the probe in the working channel in such a way that during coagulation the probe is kept immovable relative to the distal end of the endoscope.

* * * * *